(12) United States Patent
Matsushita et al.

(10) Patent No.: US 8,772,564 B2
(45) Date of Patent: Jul. 8, 2014

(54) METHOD OF PRODUCING SYNTHETIC ZEOLITE CATALYST AND METHOD OF PRODUCING HIGH-PURITY PARAXYLENE WITH A CATALYST PRODUCED BY SUCH A METHOD

(75) Inventors: Koichi Matsushita, Toda (JP);
Chikanori Nakaoka, Toda (JP);
Norikazu Nishiyama, Toyonaka (JP)

(73) Assignee: JX Nippon Oil & Energy Corporation, Tokyo (JP)

( * ) Notice: Subject to any disclaimer, the term of this patent is extended or adjusted under 35 U.S.C. 154(b) by 349 days.

(21) Appl. No.: 13/119,825

(22) PCT Filed: Sep. 29, 2009

(86) PCT No.: PCT/JP2009/066952
§ 371 (c)(1),
(2), (4) Date: Mar. 18, 2011

(87) PCT Pub. No.: WO2010/041573
PCT Pub. Date: Apr. 15, 2010

(65) Prior Publication Data
US 2011/0201863 A1    Aug. 18, 2011

(30) Foreign Application Priority Data

Oct. 9, 2008  (JP) .................................. 2008-262943

(51) Int. Cl.
*C07C 2/68*  (2006.01)
*B01J 29/06*  (2006.01)

(52) U.S. Cl.
USPC ........... 585/467; 585/470; 585/477; 585/828; 502/4; 502/60; 502/63; 502/64; 502/69; 502/71

(58) Field of Classification Search
USPC .......... 502/4, 60, 63, 64, 67, 69, 71; 585/467, 585/470, 477, 828
See application file for complete search history.

(56) References Cited

U.S. PATENT DOCUMENTS 4,465,886 A * 8/1984 Rodewald ...................... 585/467
5,753,014 A * 5/1998 Van Rijn ........................... 96/12

6,177,373 B1 * 1/2001 Sterte et al. ....................... 502/4
6,811,684 B2   11/2004 Mohr et al.
2004/0198586 A1  10/2004 Mohr et al.

FOREIGN PATENT DOCUMENTS

JP  A-2001-504084  3/2001
JP  A-2003-500189  1/2003
JP  A-2003-62466   3/2003

OTHER PUBLICATIONS

Miyamoto et al., Zeolite Hifuku Shokubai o Mochiita Hannobutsu Oyobi Seiseibutsu Sentakuteki Hanno, Nov. 29, 2003, Zeolite Kenkyu Happyokai Koen Yokoshu, vol. 20th, p. 67(B27).*
Lobo et al., "Structure-Direction in Zeolite Synthesis," *Journal of Inclusion Phenomena and Molecular Recognition in Chemistry*, 1995, pp. 47-78, vol. 21, Kluwer Academic Publishers, the Netherlands.
Miyamoto et al., "Silicalite/ZSM-5 Zeolite Composite o Mochiita p-Xylene no Sentakuteki Gosei," *Dai 98 Kai Shokubai Toronkai Toronkai A Yokoshu*, Sep. 26, 2006, p. 383, No. 4I 12 (w/ English abstract).
Miyamoto et al., "Zeolite Hifuku Shokubai o Mochiita Hannobutsu Oyobi Seiseibutsu Sentakuteki Hanno," *Zeolite Kenkyu Happyokai Koen Yokoshu*, Nov. 29, 2004, p. 67, vol. 20, No. B27 (w/ English abstract).
International Search Report for International Patent Application No. PCT/JP2009/066952, mailed on Jan. 12, 2010 (w/ English translation).

\* cited by examiner

*Primary Examiner* — Elizabeth Wood
(74) *Attorney, Agent, or Firm* — Oliff PLC

(57) ABSTRACT

This invention relates to a method wherein a high-purity paraxylene can be produced efficiently by using a catalyst having a molecular sieving action (or shape selectivity) and being excellent in the catalytic activity without isomerization and adsorption-separation steps. More particularly, it relates to a method of producing a high-purity paraxylene, characterized in that MFI type zeolite having a primary particle size of not more than 100 μm, a structure defining agent and silica material having an average particle size of not less than 10 nm but less than 1.0 μm are used as a starting material, and a synthetic zeolite catalyst produced by subjecting the MFI type zeolite to a coating treatment with an aqueous solution obtained by mixing so as to satisfy X×Y<0.05 (wherein X is a concentration of the silica material (mol %) and Y is a concentration of the structure defining agent (mol %)) is used in the alkylation or disproportionation of at least one of benzene and toluene as a starting material.

5 Claims, 1 Drawing Sheet

METHOD OF PRODUCING SYNTHETIC ZEOLITE CATALYST AND METHOD OF PRODUCING HIGH-PURITY PARAXYLENE WITH A CATALYST PRODUCED BY SUCH A METHOD

TECHNICAL FIELD

This invention relates to a method of producing a synthetic zeolite catalyst coated with a monocrystalline silicate as well as a method of producing a high-purity paraxylene with a catalyst produced by the above method, and more particularly to a method of producing a high-purity paraxylene efficiently.

RELATED ART

Among aromatic compounds, xylenes are very important compounds as a starting material for producing terephthalic acid, isophthalic acid, orthophthalic acid and so on for the formation of polyesters. These xylenes are produced, for example, by transalkylation, disproportionation or the like of toluene. However, p-xylene, o-xylene and m-xylene are existent in the resulting product as a structural isomer. Terephthalic acid obtained by oxidation of p-xylene is used as a main material for polyethylene terephthalate, and phthalic anhydride obtained from o-xylene is used as a starting material for plasticizer and the like, and isophthalic acid obtained from m-xylene is used as a main material for unsaturated polyesters and the like. Therefore, it is demanded to develop a method of separating these structural isomers from the product efficiently.

However, there is a little difference in the boiling point among p-xylene (boiling point: 138° C.), o-xylene (boiling point: 144° C.) and m-xylene (boiling point: 139° C.), so that it is difficult to separate these isomers by the usual distillation method. As the method of separating these isomers, there are a super-cold separation method wherein xylene mixture including p, o- and m-isomers is subjected to a precision distillation and thereafter p-xylene having a high melting point is separated by crystallization through cooling, a method wherein p-xylene is separated by adsorption with a zeolite-based adsorbent having a molecular sieving action, and so on.

In the method of selectively separating p-xylene by super-cold separation, the crystallization through cooling should be conducted after the precision distillation of the xylene mixture including the structural isomers, so that there are problems that steps become multi-stages and complicated and the precision distillation and crystallization step through cooling cause the increase of production cost, and so on. For this end, the adsorption separation method is widely performed instead of the above method at the present. The latter method is a system in which the starting xylene mixture is moved through an adsorption tower filled with an adsorbent, during which paraxylene having a stronger adsorption force than those of the other isomers is adsorbed and separated from the other isomers. Subsequently, paraxylene is drawn out from the system through a desorbing agent and desorbed and separated from the desorbed liquid by distillation. As a practical process are mentioned PAREX method by UOP, AROMAX method by Toray Industries, Ltd. and so on. This adsorption separation method is high in the recovery and purity of paraxylene as compared with the other separation methods, but it is required to separate and remove the desorbing agent for removing paraxylene from the absorbent since the absorption and desorption are sequentially repeated in the adsorption tower comprising pseudo-moving beds of 10-odd stages, and hence the operation efficiency is never good in the high purification of paraxylene.

On the other hand, there are some attempts for improving the efficiency of the adsorption separation method for paraxylene, and also a method of conducting the separation while reacting with a catalyst having a separation function is disclosed. For example, Patent Document 1 discloses a zeolite-combined zeolite catalyst comprising a first zeolite crystal with a catalytic activity and a second zeolite crystal with a molecular sieving action. In the zeolite-combined zeolite catalyst disclosed in Patent Document 1, however, the second zeolite crystal with the molecular sieving action forms a continuous phase matrix or bridge and the ratio of the first-zeolite crystal with the catalytic activity occupied in the zeolite-combined zeolite catalyst becomes small and hence the deterioration of the catalytic activity is caused, but also when the second zeolite crystal with the molecular sieving action forms the continuous phase matrix, the permeation resistance of the molecule selected becomes too large, and it tends to deteriorate the molecular sieving action. Further, the second zeolite crystal plays the role of a binder (carrier) without using a binder (carrier) for shape holding, so that the zeolite-combined zeolite catalyst is obtained by aggregating or clumping the first zeolite crystal with the second zeolite crystal once. The aggregated or clumped catalyst is pulverized in use, but the second zeolite crystal is peeled off by the pulverization to expose a part of the first zeolite crystal, which causes the deterioration of the molecular sieving action.

Also, Patent Document 2 discloses a method of coating solid acid catalyst particles with zeolite crystal having a molecular sieving action. In this method, however, an average particle size of the catalyst particles is 0.3-3.0 mm, so that the reaction site required for the target reaction or specific surface area of the catalyst is very small. As a result, such a method is insufficient in the reaction efficiency and is never high in the toluene conversion and selectivity of paraxylene, so that it can not be used industrially.

PRIOR ART ARTICLE

Patent Document

Patent Document 1: JP-A-2001-504084
Patent Document 2: JP-A-2003-62466

SUMMARY OF THE INVENTION

Problems to be Solved by the Invention

As mentioned above, the conventional techniques do not provide a method of efficiently producing a high-purity paraxylene without complicated steps such as isomerization-adsorption separation steps, and a useful catalyst used therefor. Particularly, a crystal phase of a modifying agent is not mentioned when modifying the surface of the catalyst.

The invention is made in light of the above circumstances and is to provide a method wherein a high-purity paraxylene can be produced efficiently by using a novel catalyst having a molecular sieving action (or shape selectivity) and an excellent catalyst activity without conducting isomerization-adsorption separation steps.

Means for Solving Problems

The inventors have made various investigations and found an epoch-making method of producing paraxylene in which the separation is made easy by selecting an optimal catalyst without substantially including impurities. In the invention, only an isomer having a specified structure of a product generated inside catalyst particles passes selectively through a monocrystalline silicate film having a molecular sieving action, so that the selectivity of isomer having a specified structure can be enhanced without deteriorating the activity of the catalyst, and conversely only the isomer having the specified structure can be selectively penetrated into the inside of the catalyst particles having a catalyst activity to cause a selective (specific) reaction inside the catalyst particles. As a result, a high-purity paraxylene can be produced efficiently according to the invention.

That is, the invention is as follows:

(1) A method of producing a synthetic zeolite catalyst by coating MFI type zeolite having a primary particle size of not more than 100 μm with a monocrystalline silicate, wherein at least MFI type zeolite, a structure defining agent and a silica material having an average particle size of not less than 10 nm but less than 1.0 μm are used as a starting material, and the MFI type zeolite is subjected to a coating treatment with an aqueous solution obtained by mixing so as to satisfy X×Y<0.05 (wherein X is a concentration of the silica material (mol %) and Y is a concentration of the structure defining agent (mol %)).

(2) A method of producing a synthetic zeolite catalyst according to the item (1), wherein the monocrystalline silicate is silicalite.

(3) A method of producing a high-purity paraxylene, wherein a synthetic zeolite catalyst produced by a production method according to the item (1) or (2) is used when at least one of benzene and toluene as a starting material is subjected to an alkylation or a disproportionation.

(4) A method of producing a high-purity paraxylene according to the item (3), wherein a toluene conversion is not less than 30 mol %, and a selectivity of paraxylene in an aromatic hydrocarbon having a carbon number of 8 is not less than 97.5 mol %.

Moreover, the structure defining agent according to the invention is a reagent defining a zeolite structure (e.g. MFI or the like) during hydrothermal synthesis as exemplified in R. F. Lobo et al., Phenomena and Molecular Recognition in Chem., 21, 47 (1995), which is also called as a template or mold molecule. It is mainly an organic compound of quaternary ammonium type.

Effect of the Invention

The catalyst particles used in the invention can be preferably used in the selective production of an isomer having a specified structure by utilizing a molecular sieving action because individual particles of MFI type zeolite are coated over their surfaces with the monocrystalline silicate film having a molecular sieving action by selecting a ratio of the specified silica material to the structure defining agent. In particular, ZSM-5 having MFI structure is coated with a monocrystalline silicalite having the similar structure, whereby the shape selectivity of paraxylene can be given to the catalyst particles at a minimal modifying amount. Thus, there can be provided an excellent catalyst for producing an industrially useful paraxylene selectively without lowering the conversion.

BEST MODE FOR CARRYING OUT THE INVENTION

[Catalyst]

Figure 1:
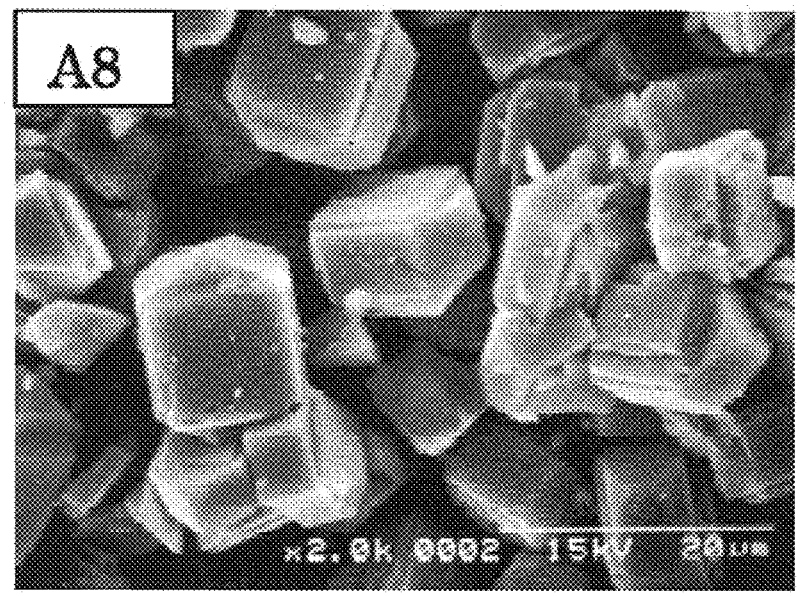
FIG. 1 is an SEM photograph of a catalyst A8 (zeolite catalyst coated with single crystal silicate).

In the method of producing a high-purity paraxylene according to the invention is used a catalyst obtained by coating MFI type zeolite having a primary particle size of not more than 100 μm with a monocrystalline silicate. The zeolite with the MFI structure used as a nucleus for the catalyst is excellent in the catalyst performance on the reaction for producing paraxylene through reaction between aromatic hydrocarbons or between aromatic hydrocarbon and alkylation agent. As the MFI type zeolite is particularly preferable ZSM-5. This zeolite can distinguish paraxylene from orthoxylene or metaxylene having a molecular size slightly larger than that of paraxylene because it has a pore opening of 0.5-0.6 nm which is same as minor axis of paraxylene molecule, and is effective in the case of producing target paraxylene.

The MFI type zeolite as a nucleus for the catalyst has a primary particle size of not more than 100 μm. When the particle size of the MFI type zeolite exceeds 100 μm, it can not be used industrially because the diffusion resistance becomes larger and the conversion of the starting aromatic hydrocarbon becomes lower. Moreover, as the particle size of the MFI type zeolite used is made smaller, the influence of diffusion inside the pores can be mitigated, so that it is preferably not more than 50 μm, more preferably not more than 20 μm, most preferably not more than 10 μm.

Also, a silica/alumina ratio in the MFI type zeolite is preferably not less than 30 but not more than 10,000, more preferably not less than 50 but not more than 5,000. When the silica/alumina ratio is less than 30, it is difficult to stably hold the MFI structure, while when it exceeds 10,000, the amount of an acid being a reaction active site becomes undesirably small.

The catalyst used in the invention is formed by coating the aforementioned MFI type zeolite with a monocrystalline silicate, in which the monocrystalline silicate develops a molecular sieving action. The monocrystalline silicate film having the molecular sieving action (zeolite film) is preferable to have the structure similar to that of the MFI type zeolite as the nucleus and to be continuous in the pores. As a method of confirming the continuity of the pores are mentioned a method of measuring diffusion rate of hydrocarbon in accordance with the pore opening, a method of using a Hammet's indicator in accordance with the pore opening, and so on. Further, the monocrystalline silicate is desirable to be inactive to disproportionation reaction and alkylation reaction, and is particularly preferable to be pure silica zeolite containing no alumina component (silicalite-1). Since silicalite-1 is very few in the acid point, it is particularly preferable for inactivating the surface after the coating. Moreover, silicon in the monocrystalline silicate may be partially replaced with another element such as gallium, germanium, phosphorus, boron or the like. Even in the latter case, it is important to maintain the surface at the inactivated state.

The amount of the monocrystalline silicate by weight is preferably not less than 10 parts, more preferably not less than 20 parts but preferably not more than 100 parts, more preferably not more than 70 parts per 100 parts of the MFI type zeolite as a nucleus. When the amount of the monocrystalline silicate is less than 10 parts by weight per 100 parts by weight of the MFI type zeolite, the molecular sieving action of the monocrystalline silicate film can not be developed sufficiently, while when it exceeds 100 parts by weight, the ratio of the MFI type zeolite in the catalyst becomes too small to cause the deterioration of the catalyst activity, but also the resistance of a body to be treated such as starting materials, products or the like passing through the monocrystalline silicate film may become too large. The thickness of the monocrystalline silicate film is preferably not less than 0.01 μm, more preferably not less than 0.05 μm, but is preferably not more than 50 μm, more preferably not more than 10 μm. When the thickness of the monocrystalline silicate film is less than 0.01 μm, the molecular sieving action of the monocrystalline silicate film can not be developed sufficiently, while when it exceeds 50 μm, the monocrystalline silicate thickness is too thick and the resistance of the body to be treated such as starting materials, products or the like passing through the monocrystalline silicate film becomes too large.

In the invention, as a method of coating full surfaces of individual particles of the MFI type zeolite with the monocrystalline silicate film can be used the conventional method for the preparation of zeolite film such as hydrothermal synthesis method or the like as mentioned below. For example, a silica source such as amorphous silica, amorphous silica, fumed silica, colloidal silica or the like, a structure defining agent such as tetrapropyl ammonium hydroxide or the like and a mineralizer such as hydroxide of an alkali metal or an alkaline earth metal, and so on are first dissolved in water or ethanol in accordance with the composition of the target monocrystalline silicate film to prepare a sol for the formation of the monocrystalline silicate film.

At this moment, the monocrystalline silicate film can be formed by using the silica material and the structure defining agent at an appropriate ratio. In this case, when the concentration of the silica material is X (mol %) and the concentration of the structure defining agent is Y (mol %), an aqueous solution of the mixture satisfying a relation of $X \times Y < 0.05$ is used for the coating treatment. When the value of $X \times Y$ is not less than 0.05, the crystallization rate is too fast, and hence the desired coating treatment is not carried out efficiently, and the monocrystal structure is hardly obtained.

The silica material used is desirable to have an average particle size of not less than 10 nm but less than 1.0 μm, preferably not less than 20 nm but less than 0.5 μm for the purpose of properly controlling a rate of silica eluted to the aqueous solution of the coating. When the average particle size of the silica material is less than 10 nm, the monocrystal structure is hardly obtained due to the crystal growth between the mutual silica materials, while when it is not less than 1.0 μm, the formation of the film itself is difficult.

Similarly, the aqueous solution is desirable to have pH of not less than 7 but less than 10. When the pH of the aqueous solution is outside the above range, the reaction of forming the silicate film is not promoted sufficiently.

Then, the individual particles of the MFI type zeolite are immersed into the sol for the formation of the monocrystalline silicate film, or the sol for the formation of the monocrystalline silicate film is applied to the individual particles of the MFI type zeolite, whereby the full surfaces of the individual particles of the MFI type zeolite are treated with the sol for the formation of the monocrystalline silicate film. Next, hydrothermal treatment is conducted to form a monocrystalline silicate film on each of the full surfaces of the individual particles of the MFI type zeolite. The hydrothermal treatment can be conducted by immersing the particles of the MFI type zeolite treated with the sol for the formation of the monocrystalline silicate film into hot water or into hot water in an autoclave or leaving them to stand in a heated steam. Also, the hydrothermal treatment may be conducted at a state of immersing the particles of the MFI type zeolite into the sol for the formation of the monocrystalline silicate film. In the latter case, the autoclave including the particles of the MFI type zeolite and the sot for the formation of the monocrystalline silicate film therein may be directly placed in an oven and then heated.

The hydrothermal treatment is carried out at a temperature of preferably not lower than 120° C., more preferably not lower than 150° C. but preferably not higher than 250° C., more preferably not higher than 200° C. for a time of preferably not less than 0.5 hour, more preferably not less than 1 hour but preferably not more than 48 hours, more preferably not more than 36 hours. After the hydrothermal treatment, the particles of the MFI type zeolite are taken out and dried and further subjected to a heat treatment, whereby the monocrystalline silicate film is fired. The firing may be carried out by raising the temperature at a temperature rising rate of 0.1-10° C./min, if necessary, and thereafter conducting the heat treatment at a temperature of 500-700° C. for 2-10 hours.

[Disproportionation/Alkylation Reaction of Aromatic Hydrocarbon]

The method of producing paraxylene according to the invention is characterized in that paraxylene is selectively produced in the presence of the aforementioned catalyst by the reaction between mutual aromatic hydrocarbons (disproportionation) or the reaction between aromatic hydrocarbon and alkylation agent (alkylation).

As the starting aromatic hydrocarbon are mentioned benzene and toluene. Moreover, the starting aromatic hydrocarbon may include a hydrocarbon compound other than benzene and toluene. However, since paraxylene is a target product, the starting material is not desirable to contain metaxylene or orthoxylene.

As the alkylation agent used in the invention are mentioned methanol, dimethyl ether and the like. They may be commercially available, but methanol or dimethyl ether made from synthetic gas such as mixed gas of hydrogen and carbon monoxide, or dimethyl ether produced through dehydration reaction of methanol may be the starting material. Moreover, as a potential impurity existing in benzene, toluene, methanol and dimethyl ether are mentioned water, an olefin, a sulfur compound and a nitrogen compound, but they are desirable to be small. As a desirable content, the water is not more than 200 weight ppm, more preferably not more than 100 weight ppm, and the olefin is not more than 1% by weight, more preferably not more than 0.5% by weight, and the sulfur compound and nitrogen compound are not more than 1 weight ppm, more preferably not more than 0.1 weight ppm.

The ratio of alkylation agent to aromatic hydrocarbon in the alkylation reaction is preferably 5/1-1/20, more preferably 2/1-1/10, most preferably 1/1-1/5 as a molar ratio of methyl group to aromatic hydrocarbon. When the alkylation agent is extremely large as compared with the aromatic hydrocarbon, undesirable reaction between mutual alkylation agents is promoting, resulting in the possibility that caulking is caused to deteriorate the catalyst. On the other hand, when the alkylation agent is extremely small as compared with the aromatic hydrocarbon, the alkylation reaction to the aromatic hydrocarbon is not substantially promoted, and hence when toluene is used as the aromatic hydrocarbon, the disproportionation reaction of toluene becomes promoted.

The disproportionation reaction or alkylation reaction is desirable to be carried out by feeding the starting aromatic hydrocarbon at a liquid hourly space velocity (LHSV) of not less than 0.01 h$^{-1}$, more preferably not less than 0.1 h$^{-1}$ but not more than 10 h$^{-1}$, more preferably not more than 5 h$^{-1}$ to contact with the above catalyst. The conditions of the disproportionation reaction or alkylation reaction are not particularly limited, but the reaction temperature is preferably not lower than 200° C., more preferably not lower than 230° C., most preferably not lower than 260° C. but preferably not higher than 550° C., more preferably not higher than 530° C., most preferably not higher than 510° C., and the pressure is preferably not less than atmospheric pressure, more preferably not less than 0.1 MPaG, most preferably not less than 0.5 MPaG but preferably not more than 10 MPaG, more preferably not more than 5 MPaG. In the alkylation reaction, an inert gas such as nitrogen or helium or hydrogen for controlling the caulking may be circulated or pressurized. Moreover, when the reaction temperature is too low, the activation of the aromatic hydrocarbon or alkylation agent is insufficient and the active site is poisoned with water generated by the reaction, and hence the conversion of the starting aromatic hydrocarbon is low, while when the reaction temperature is too high, a lot of energy is consumed but also it tends to shorten the catalyst service life.

As the methylation reaction of toluene is promoted in the presence of the aforementioned catalyst, it is assumed to generate orthoxylene and metaxylene as a structural isomer, unreacted toluene, alkylbenzenes promoting methylation and having a carbon number of not less than 9 in addition to paraxylene as a target product. At this moment, the ratio of paraxylene component among aromatic hydrocarbons having a carbon number of 8 is preferable to become higher, and is preferably not less than 95 mol % at one-stage step of the reaction, more preferably not less than 97.5 mol %, further preferably not less than 99.7 mol %, particularly preferably not less than 99.8 mol %, most preferably not less than 99.9 mol %.

On the other hand, it is preferable that products having a carbon number other than 8 become less. The residual amounts of benzene having a carbon number of 6 and toluene having a carbon number of 7 are largely depended upon the reaction temperature and the mixing ratio with the alkylation agent, but when the actual process is assumed, these amounts as a residual ratio are preferably not more than 70 mol %, more preferably not more than 50 mol %, most preferably not more than 30 mol %. In other words, the amounts as a conversion is preferably not less than 30 mol %, more preferably not less than 50 mol %, most preferably not less than 70 mol %. When the residual ratio is high or when the conversion is low, or when the conversion is low, it is required to again return the unreacted toluene to the starting material line for the reaction, which causes a demerit of largely lowering the production efficiency.

Since aromatic hydrocarbons having a carbon number of not less than 9 are easily produced as the ratio of the alkylation agent as a reaction condition becomes higher, it is preferable that the ratio of the alkylation agent is not extremely high as previously mentioned. The total content of the aromatic hydrocarbons having a carbon number of not less than 9 in the reaction product is preferably not more than 5 mol %, more preferably not more than 1 mol %, most preferably not more than 0.1 mol %. When the content of the aromatic hydrocarbons having a carbon number of not less than 9 is large, the separation through distillation or the like takes lots of energy, so that the content is particularly preferable to be not more than 0.1 mol %.

The reaction product may be separated and concentrated by the existing method. In the invention, however, paraxylene having an extremely high purity is obtained selectively, so that it is possible to conduct isolation by only a simple distillation method. That is, the product can be divided by a simple distillation into a fraction having a lower boiling point than that of unreacted benzene or toluene, a high-purity paraxylene and a fraction having a higher boiling point than that of paraxylene. When the amount of the fraction having a higher boiling point than that of paraxylene is very low, the high-purity paraxylene can be isolated only by distilling off a light fraction. Moreover, the unreacted toluene may be again reacted as a starting material.

EXAMPLES

The following examples are given in illustration of the invention and are not intended as limitations thereof.

(Treatment for Coating Catalyst)

<Preparation of Catalysts A1-A8>

Hydrothermal synthesis is carried out in an autoclave at 180° C. for 24 hours by using 15 g of a solution obtained by properly mixing non-aqueous fumed silica having an average particle size of 112 nm (made by Wako Pure Chemical Industries Ltd., AEROSIL 200), tetrapropylammonium hydroxide (TPAOH), ethanol and deionized water so as to provide a ratio as shown in Table 1 with respect to 0.3 g of H-ZSM-5 (particle size: 10 μm). The resulting product is washed, filtered and fired at 600° C. for 5 hours to obtain catalysts A1-A8. Moreover, the catalyst A7-2 in Table 1 is obtained by further subjecting the catalyst A7-1 to a coating treatment, and the weight increment represents a ratio of weight increased by the coating treatment based on the weight of H-ZSM-5. As a result, a polycrystalline type coating phase is confirmed for the catalyst A1, while a monocrystalline type coating phase is confirmed for the other catalysts as measured by SEM. In FIG. 1 is shown an SEM photograph of the catalyst A8 (zeolite catalyst coated with monocrystalline silicate). Moreover, the average particle size is measured in a 20% aqueous dispersion with a laser diffraction particle size distribution meter (LA-920) made by HORIBA Ltd.

TABLE 1

| | Catalyst | | | | |
|---|---|---|---|---|---|
| | A1 | A6 | A7-1 | A7-2 | A8 |
| | Charge amount | | | | |
| fumed silica (mol) | 2 | 0.5 | 0.5 | 0.5 | 0.5 |
| TPAOH (mol) | 0.12 | 0.06 | 0.06 | 0.06 | 0.03 |

TABLE 1-continued

| | Catalyst | | | | |
|---|---|---|---|---|---|
| | A1 | A6 | A7-1 | A7-2 | A8 |
| ethanol (mol) | 8 | 8 | 8 | 8 | 8 |
| water (mol) | 120 | 120 | 120 | 120 | 120 |
| | Mol % | | | | |
| fumed silica (mol %), X | 1.54 | 0.39 | 0.39 | 0.39 | 0.39 |
| TPAOH (mol %), Y | 0.09 | 0.09 | 0.05 | 0.05 | 0.02 |
| ethanol (mol %) | 6.15 | 6.21 | 6.22 | 6.22 | 6.22 |
| water (mol %) | 92.2 | 93.3 | 93.3 | 93.3 | 93.3 |
| X × Y | 0.139 | 0.035 | 0.020 | 0.020 | 0.008 |
| Weight increment (%) | +167 | +40 | +51 | — | +36 |
| Crystal form of coating phase | polycrystal | monocrystal | monocrystal | monocrystal | monocrystal |

<Preparation of Catalysts T1-T7>

Figure 2:
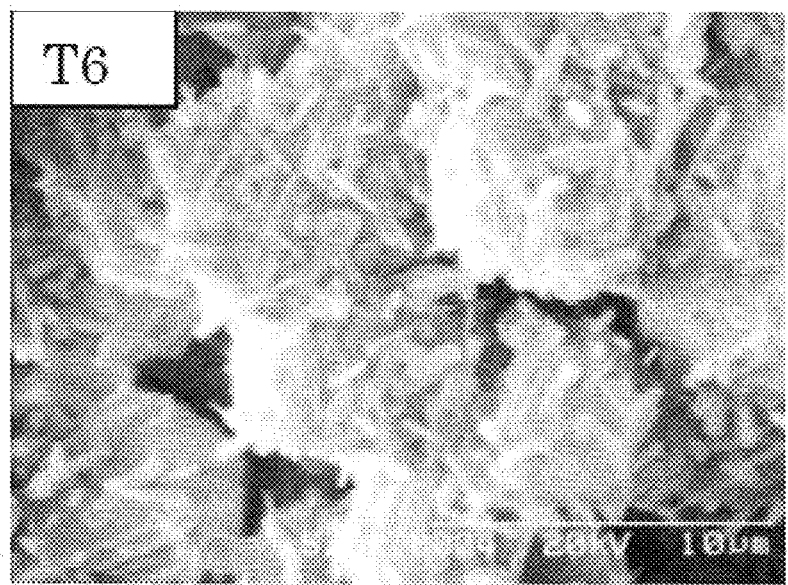
FIG. 2 is an SEM photograph of catalyst T6 (zeolite catalyst coated with polycrystalline silicate).

Catalysts T1-T7 are obtained under the same conditions as mentioned above except that water-soluble tetraethoxy silane (TEOS) (particle size in solution: less than 10 nm) is used instead of fumed silica in the preparation of the mixed solution according to charge amounts shown in Table 2. As a result, it is confirmed that all of these catalysts indicate polycrystalline type coating phase as measured by SEM. In FIG. 2 is shown an SEM photograph of the catalyst T6 (zeolite catalyst coated with polycrystalline silicate).

TABLE 2

| | Catalyst | | | |
|---|---|---|---|---|
| | T1 | T4 | T6 | T7 |
| | Charge amount | | | |
| TEOS (mol) | 2 | 1 | 0.5 | 0.5 |
| TPAOH (mol) | 0.5 | 0.06 | 0.06 | 0.03 |
| ethanol (mol) | 8 | 8 | 8 | 8 |
| water (mol) | 120 | 120 | 120 | 120 |
| | Mol % | | | |
| TEOS (mol %), X | 1.53 | 0.77 | 0.39 | 0.39 |
| TPAOH (mol %), Y | 0.38 | 0.05 | 0.05 | 0.02 |
| ethanol (mol %) | 6.13 | 6.20 | 6.22 | 6.22 |
| water (mol %) | 92.0 | 93.0 | 93.0 | 93.4 |
| X × Y | 0.581 | 0.039 | 0.020 | 0.008 |
| Weight increment (%) | +180 | +71 | +44 | +35 |
| Crystal form of coating phase | polycrystal | polycrystal | polycrystal | polycrystal |

Example 1

An alkylation of toluene is carried out by diluting 0.05 g of a catalyst A6 with glass beads of 1.0 mmϕ and filling them in a fixed layer reaction vessel of 4 mm in inner diameter to form a catalyst layer of 20 mm in length while passing helium gas thereinto at 400° C. and an atmospheric pressure under conditions that a ratio of methanol to toluene is 1.0 mol/mol, LHSV is 2.0 h$^{-1}$. After 1 hour from the start of the reaction, the product discharged from an outlet of the reaction vessel is analyzed by a gas chromatography to measure a ratio of each isomer in the product. The results are shown in Table 3, and the measuring conditions of the gas chromatography are shown below.

Measuring apparatus: GC-2014 made by Shimadzu Corporation

Column: capillary column Xylene Master, inner diameter of 0.32 mm, 50 m

Temperature condition: column temperature of 50° C., temperature rising rate of 2° C./min, temperature of detector (FID) of 250° C.

Carrier gas: helium

Toluene conversion (mol %)=100−(mol of residual toluene/mol of toluene in starting material)×100

Selectivity or paraxylene (mol %)=(mol of resulting paraxylene/mol of resulting C8 aromatic hydrocarbon)×100

Examples 2-4, Comparative Examples 1-6

The alkylation of toluene us carried out under the same conditions as in Example 1 except for the use of catalysts as shown in Table 3. The results are shown in Table 3. Moreover, the catalyst used in Comparative Example 6 is H-ZSM-5 not subjected to the aforementioned coating treatment.

TABLE 3

| | Example 1 | Example 2 | Example 3 | Example 4 | Comparative Example 1 | Comparative Example 2 | Comparative Example 3 | Comparative Example 4 | Comparative Example 5 | Comparative Example 6 |
|---|---|---|---|---|---|---|---|---|---|---|
| Catalyst | A6 | A7-1 | A7-2 | A8 | A1 | T1 | T4 | T6 | T7 | Uncoated |
| Conversion of toluene (mol %) | 36.5 | 39.4 | 33.3 | 38.4 | 35.3 | 33.2 | 37.7 | 46.4 | 40.8 | 53.2 |
| Selectivity of paraxylene (mol %) | 97.6 | 98.2 | 98.7 | 99.3 | 97.0 | 96.8 | 93.2 | 94.0 | 82.2 | 75.3 |
| Product composition (mol %) | | | | | | | | | | |
| benzene | 0.00 | 0.00 | 0.00 | 0.00 | 0.00 | 0.00 | 0.00 | 0.00 | 0.00 | 0.00 |
| ethylbenzene | 0.22 | 0.17 | 0.13 | 0.15 | 0.16 | 0.12 | 0.36 | 0.12 | 0.16 | 0.18 |
| paraxylene | 29.66 | 34.26 | 28.99 | 31.38 | 30.17 | 25.04 | 29.94 | 40.18 | 28.87 | 31.74 |
| metaxylene | 0.32 | 0.27 | 0.11 | 0.00 | 0.47 | 0.48 | 1.27 | 1.45 | 4.29 | 6.33 |
| orthoxylene | 0.19 | 0.20 | 0.14 | 0.08 | 0.31 | 0.22 | 0.55 | 1.00 | 1.79 | 3.93 |
| paraethyl toluene | 5.28 | 3.29 | 2.95 | 5.73 | 3.31 | 3.96 | 4.41 | 2.11 | 3.01 | 4.05 |
| metaethyl toluene | 0.10 | 0.06 | 0.04 | 0.03 | 0.09 | 0.22 | 0.28 | 1.29 | 0.37 | 1.61 |
| orthoethyl toluene | 0.02 | 0.00 | 0.00 | 0.00 | 0.02 | 2.92 | 0.67 | 0.27 | 1.99 | 0.01 |
| trimethyl benzene | 0.72 | 1.10 | 0.91 | 1.02 | 0.78 | 0.20 | 0.24 | 0.00 | 0.27 | 5.31 |

As seen from the examples, by using zeolite catalysts coated with a monocrystalline silicate (A6-A8) as a catalyst is selectively produced p-xylene so that the selectivity of p-xylene is as very high as not less than 97.5% as compared with a thermodynamic equilibrium composition (about 25%). Also, the resulting oil contains substantially paraxylene (boiling point: 138° C.) and aromatic hydrocarbons having a carbon number of not less than 9 (boiling point: 165-176° C.) in addition to toluene (boiling point: 110° C.) as a starting material, so that a high-concentration paraxylene can be easily obtained by distillation.

On the other hand, as shown in Comparative Examples 1-6, it can be seen that the selectivity of paraxylene is largely lowered as compared with those of the examples when zeolite catalysts coated with polycrystalline silicate (A1, T1-T7) or the uncoated catalyst is used as a catalyst.

The invention claimed is:

1. A method of producing a synthetic zeolite catalyst by coating MFI type zeolite having a primary particle size of not more than 100 μm with a monocrystalline silicate, wherein the MFI type zeolite is subjected to a coating treatment in which the MFI type zeolite is immersed into an aqueous solution obtained by mixing a structure defining agent and a silica material having an average particle size of not less than 10 nm but less than 1.0 μm so as to satisfy X×Y<0.05 (wherein X is a concentration of the silica material (mol %) and Y is a concentration of the structure defining agent (mol %)), then subjected to a hydrothermal treatment at a temperature of 120° C. to 250° C. for 0.5 hour to 48 hours and further fired.

2. The method of producing a synthetic zeolite catalyst according to claim 1, wherein the monocrystalline silicate is silicalite.

3. A method of producing a high-purity paraxylene, which comprises the step of subjecting at least one of benzene and toluene as a starting material to an alkylation or a disproportionation in the presence of a synthetic zeolite catalyst produced by a method as claimed in claim 1 at a liquid hourly space velocity of 0.01 $h^{-1}$ to 10 $h^{-1}$ and a temperature of 200° C. to 550° C.

4. The method of producing a high-purity paraxylene according to claim 3, wherein a conversion of toluene is not less than 30 mol %, and a selectivity of paraxylene in aromatic hydrocarbons having a carbon number of 8 is not less than 97.5 mol %.

5. A method of producing a high-purity paraxylene, which comprises the step of subjecting at least one of benzene and toluene as a starting material to an alkylation or a disproportionation in the presence of a synthetic zeolite catalyst produced by a method as claimed in claim 2 at a liquid hourly space velocity of 0.01 $h^{-1}$ to 10 $h^{-1}$ and a temperature of 200° C. to 550° C.

* * * * *